(12) United States Patent
Spool et al.

(10) Patent No.: US 9,446,200 B2
(45) Date of Patent: Sep. 20, 2016

(54) LEVER AND GEAR FORCE MULTIPLIER MEDICATION DELIVERY SYSTEM FOR HIGH PRESSURE INJECTION SYSTEM

(75) Inventors: Ira Spool, Brookline, MA (US); Michel Bruehwiler, Newton, MA (US); Ryan Schoonmaker, Salem, MA (US); Melissa Rosen, Lynn, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1238 days.

(21) Appl. No.: 12/998,841

(22) PCT Filed: Dec. 8, 2009

(86) PCT No.: PCT/US2009/006419
§ 371 (c)(1),
(2), (4) Date: Sep. 20, 2011

(87) PCT Pub. No.: WO2010/077277
PCT Pub. Date: Jul. 8, 2010

(65) Prior Publication Data
US 2012/0004620 A1 Jan. 5, 2012

Related U.S. Application Data

(60) Provisional application No. 61/193,592, filed on Dec. 9, 2008.

(51) Int. Cl.
*A61M 5/315* (2006.01)
*A61M 5/24* (2006.01)
(52) U.S. Cl.
CPC .......... *A61M 5/31511* (2013.01); *A61M 5/24* (2013.01); *A61M 2005/3152* (2013.01)
(58) Field of Classification Search
CPC ......... A61M 5/3155; A61M 5/13551; A61M 5/31553; A61M 5/31563; A61M 5/31581; A61M 2005/31518; A61M 2005/3152; A61M 5/31511; A61M 5/31551; A61M 5/24
See application file for complete search history.

(56) References Cited

U.S. PATENT DOCUMENTS 2,669,230 A 2/1954 Smoot
2,725,877 A * 12/1955 Reiter ............... A61M 5/20
604/135

(Continued)

FOREIGN PATENT DOCUMENTS

JP 62-502876 11/1987
JP H066505415 6/1994

(Continued)

OTHER PUBLICATIONS

Supplemental European Search Report, Dated Apr. 1, 2014, 6 pages.

(Continued)

*Primary Examiner* — Kami A Bosworth
(74) *Attorney, Agent, or Firm* — Dickinson Wright PLLC

(57) ABSTRACT

A drug delivery device includes a cartridge (211) for storing a medicament and a needle (203) communicating with the cartridge (211) for injecting a medicament dose. A rack (241) is movably disposed in the cartridge (211) and is engageable with a stopper (213) for expelling the medicament dose from the cartridge (211). A lever assembly (231) has a lever arm (233) connected to a lever gear (230). The lever gear (232) is engaged with the rack (241) such that rotation of the lever arm (233) rotates the lever gear (232) during injection of the medicament dose, thereby moving the rack (241) and stopper (213) through the cartridge (211) to deliver the medicament dose.

22 Claims, 19 Drawing Sheets

(56) References Cited

U.S. PATENT DOCUMENTS

| | | | |
|---|---|---|---|
| 3,782,380 A | 1/1974 | Van Der Gaast | |
| 4,447,223 A * | 5/1984 | Kaye | A61M 37/0069 604/61 |
| 4,643,723 A | 2/1987 | Smit | |
| 4,762,515 A | 8/1988 | Grimm | |
| 4,820,287 A | 4/1989 | Leonard | |
| 5,279,585 A | 1/1994 | Balkwill | |
| 5,279,586 A | 1/1994 | Balkwill | |
| 5,549,575 A | 8/1996 | Giambattista | |
| 5,569,214 A | 10/1996 | Chanoch | |
| 5,582,598 A | 12/1996 | Chanoch | |
| 5,674,204 A | 10/1997 | Chanoch | |
| 5,921,966 A | 7/1999 | Bendek | |
| 5,944,700 A | 8/1999 | Nguyen | |
| 5,957,896 A | 9/1999 | Bendek | |
| 5,988,452 A | 11/1999 | Dent | |
| 6,074,372 A | 6/2000 | Hansen | |
| 6,096,010 A | 8/2000 | Walters | |
| 6,159,161 A * | 12/2000 | Hodosh | 600/561 |
| 6,221,053 B1 | 4/2001 | Walters | |
| 6,248,095 B1 | 6/2001 | Giambattista | |
| 6,277,099 B1 | 8/2001 | Strowe | |
| 6,537,242 B1 | 3/2003 | Palmer | |
| 6,595,956 B1 | 7/2003 | Gross | |
| 6,599,272 B1 | 7/2003 | Hjertman | |
| 6,932,794 B2 | 8/2005 | Giambattista | |
| 6,936,032 B1 | 8/2005 | Bush, Jr. | |
| 6,939,319 B1 | 9/2005 | Anstead | |
| 7,018,364 B2 | 3/2006 | Giambattista | |
| 7,169,132 B2 | 1/2007 | Bendek | |
| 2002/0007154 A1 | 1/2002 | Hansen et al. | |
| 2005/0090781 A1 | 4/2005 | Baba | |
| 2005/0165363 A1 | 7/2005 | Judson | |
| 2006/0069355 A1 * | 3/2006 | Judson et al. | 604/211 |
| 2007/0167907 A1 | 7/2007 | Deslierres | |

FOREIGN PATENT DOCUMENTS

| | | |
|---|---|---|
| JP | 2003126252 | 5/2003 |
| JP | 2004508897 | 3/2004 |
| JP | 2008538719 | 11/2008 |
| WO | 0119434 A1 | 3/2001 |
| WO | 03080160 A1 | 10/2003 |
| WO | 2007/113318 | 10/2007 |

OTHER PUBLICATIONS

Japanese Office Action Issued in JP Application No. 2011-540690 dated Sep. 24, 2013.

* cited by examiner

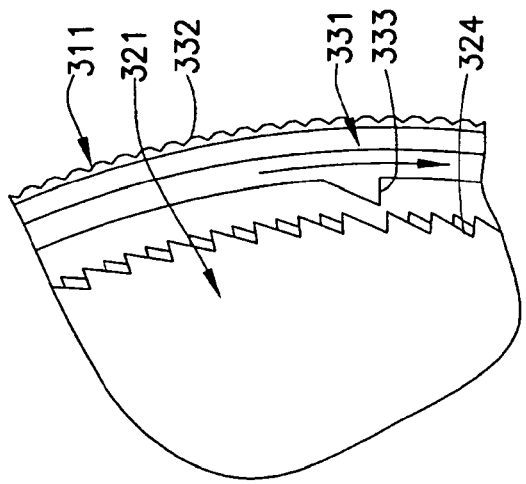
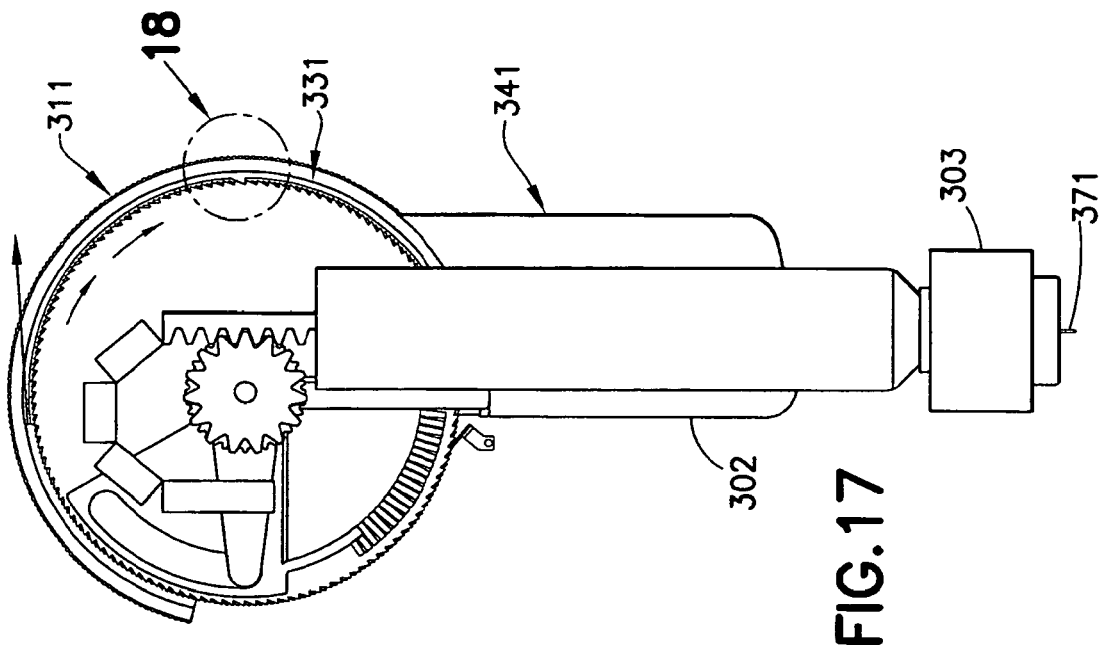

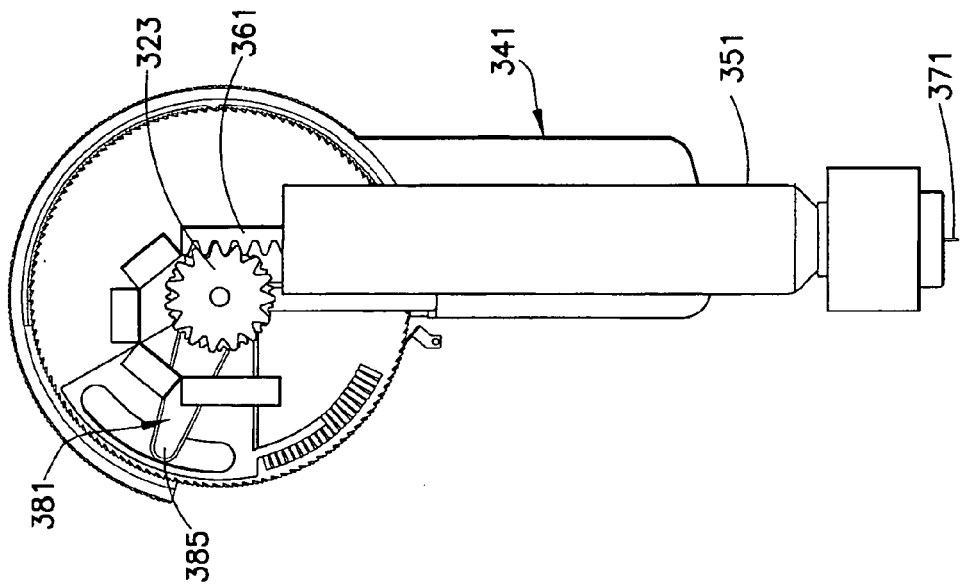
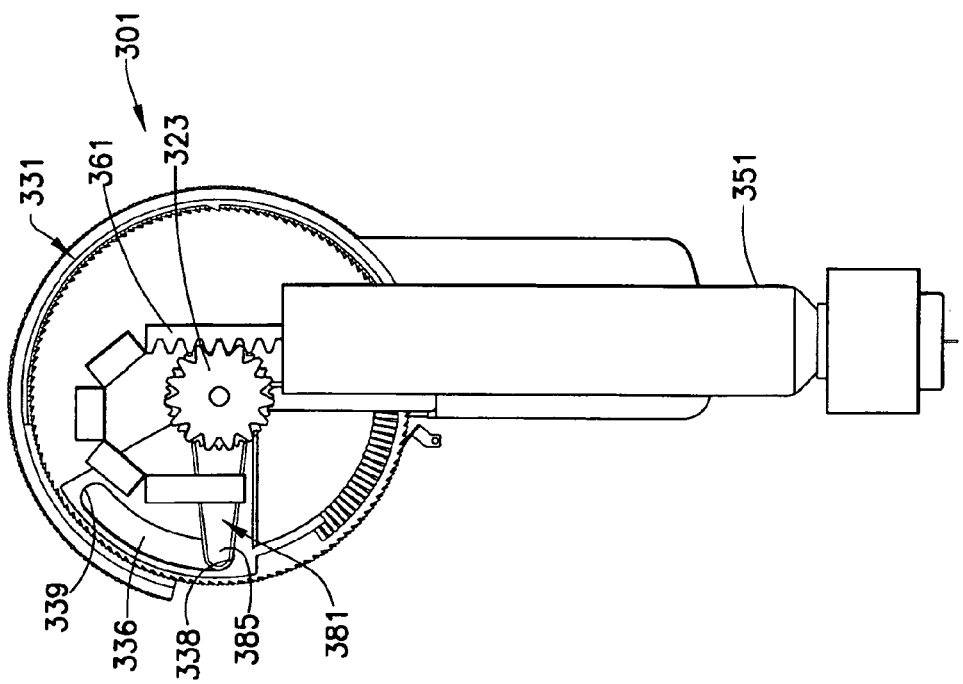

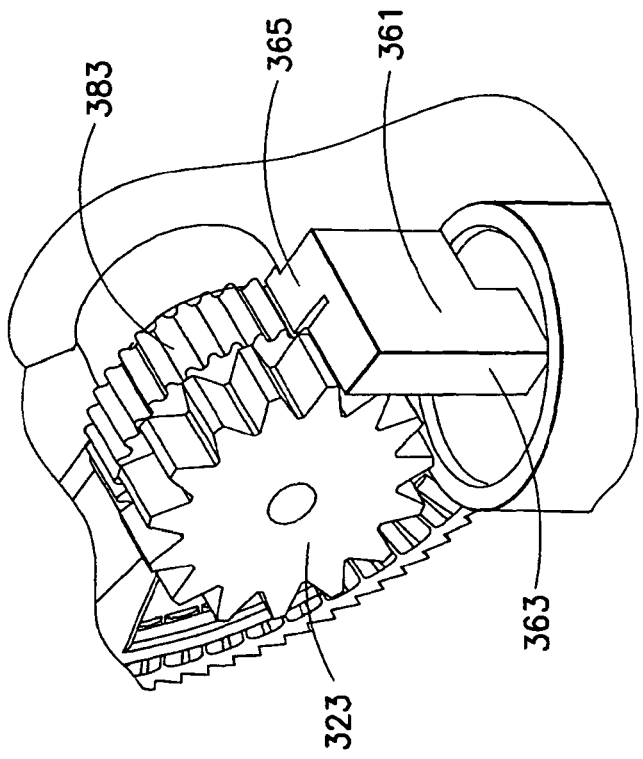
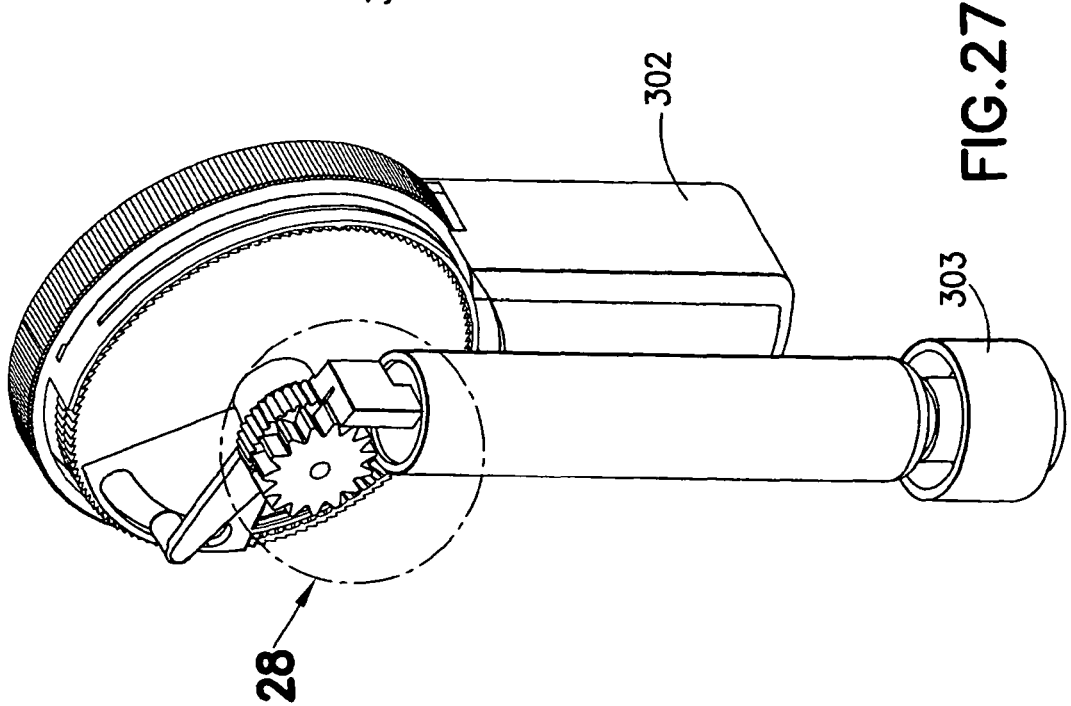

LEVER AND GEAR FORCE MULTIPLIER MEDICATION DELIVERY SYSTEM FOR HIGH PRESSURE INJECTION SYSTEM

CROSS REFERENCE TO RELATED APPLICATION

This application claims the benefit under 35 U.S.C. §119(e) of U.S. Provisional Application Ser. No. 61/193,592, filed Dec. 9, 2008, the entire content of which is hereby incorporated by reference.

FIELD OF THE INVENTION

The present invention relates generally to a drug delivery device that facilitates high pressure medication injections. More particularly, the present invention relates to a drug delivery device that uses a mechanical advantage to facilitate high pressure medication injections. Still more particularly, the present invention relates to a drug delivery device including a system of levers and gears to translate an input force into an injection force to facilitate high pressure intradermal injections.

BACKGROUND OF THE INVENTION

Insulin and other injectable medicaments are commonly given with syringes into the intradermal layer of the skin and other dense tissues. Intradermal medication injections result in faster uptake of the medication, thereby resulting in improved therapy. Such injections require higher injection pressures, upwards of 200 psi, than traditional subcutaneous injections.

Techniques and devices are known for administering an injection into the intradermal region of the skin. One method, commonly referred to as the Mantoux technique, uses a "standard" needles and syringe, i.e., a syringe typically used to administer intramuscular or subcutaneous injections. The health care provider administering the injection follows a specific procedure that requires a somewhat precise orientation of the syringe with regard to the patient's skin as the injection is administered. The health care provider must also attempt to precisely control the penetration depth of the needle into the patient's skin to ensure that it does not penetrate beyond the intradermal region. Such a technique is complicated, difficult to administer, and often may only be administered by an experienced health care professional.

As advances in understanding the delivery of drug proceeds, the use of intradermal delivery systems is expected to increase. However, use of a "standard" length needle to deliver a drug substance intradermally has its shortcomings, as noted above. Moreover, it is not possible to use a delivery device having a needle length suited for intradermal injection to aspirate a syringe with drug substance from a multi-use vial. Thus, there are shortcomings in the prior art that prevent administering an intradermal injection using a "standard" length needle and a multi-use vial. It would be advantageous to have a drug delivery device capable of accessing substances stored in multi-dose vials and delivering such substances into the intradermal region of the skin without encountering the shortcomings described above.

A conventional syringe 101 is shown in FIG. 1. The needle 103 is sufficiently long to deliver the drug to the subcutaneous region of the skin. However, a user would not be able to easily deliver the drug to the intradermal region of the skin, as discussed above.

Drug delivery pens, such as the exemplary drug delivery pen 100 shown in FIGS. 2 and 3, are designed for intradermal injections and typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the drug delivery pen 100 in a shirt pocket, purse or other suitable location and provide cover/protection from accidental needle injury.

FIG. 3 is an exploded view of the drug delivery pen 100 of FIG. 2. The dose knob/button 24 has a dual purpose and is used both to set the dosage of the medication to be injected and to inject the dosed medicament via the leadscrew 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used, such as attaching to the cartridge. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle by any suitable means, such as an interference fit or a snap fit. The outer cover 69 and the inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

The backpressure in subcutaneous injections is not very large, while the backpressure associated with intradermal injections may be many times greater than that of subcutaneous injections. Existing drug delivery pens require a large force to inject medication into the intradermal layer, thereby making the intradermal medication injection difficult. For example, the backpressure often exceeds 200 psi for an intradermal injection, while the backpressure for a subcutaneous injection is generally in the range of 30-50 psi. Thus, a need exists for a drug delivery pen that has a high mechanical advantage to facilitate an intradermal injection.

SUMMARY OF THE INVENTION

In accordance with an aspect of the present invention, a drug delivery device is provided that facilitates injecting insulin or other medicaments at high pressures.

In accordance with another aspect of the present invention, a drug delivery device has a system of levers and gears to produce sufficient force for an intradermal injection, without increasing the input force required from the user.

In accordance with another aspect of the present invention, a drug delivery device achieves mechanical advantage without requiring a secondary chamber, thereby reducing drug exposure outside of the original container.

In accordance with another aspect of the present invention, a drug delivery device is compact, thereby increasing usability and portability of the device.

Existing reusable and disposable insulin pens feature nut/screw drive mechanisms, are traditionally used for subcutaneous injections, and do not have a significant amount of mechanical advantage. To inject into an intradermal space, the user input force would be nearly 20 lbs, which is unacceptably high for insulin patients. Additionally, the components in the device can start to deform and fail at these high pressures. A drug delivery device according to an exemplary embodiment of the present invention transforms the user input into rotary motion that drives a system of gears, which have specified gear ratios, to create a mechanical advantage; thereby achieving the high pressure required for intradermal delivery. Additionally, the traditional cartridge components may be modified to withstand the injection pressure.

The lever and gear system creates the mechanical advantage that allows for a much more robust design of the individual components and critical interfaces when compared to a pen-type (screw/nut) device in which the user force and stroke of the injection motion are translated into a torque, which is then used to drive the drive screw 7 (FIGS. 2 and 3) and cartridge stopper 15 linearly forward.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which:

FIGS. 17 and 18 illustrate correcting a dose with the drug delivery device of FIGS. 10A-10B;

FIGS. 23-28 illustrate dose tracking with the drug delivery device of FIGS. 10A-10B.

Throughout the drawings, like reference numbers will be understood to refer to like parts, components and structures.

DETAILED DESCRIPTION OF THE EXEMPLARY EMBODIMENTS

Figure 1:
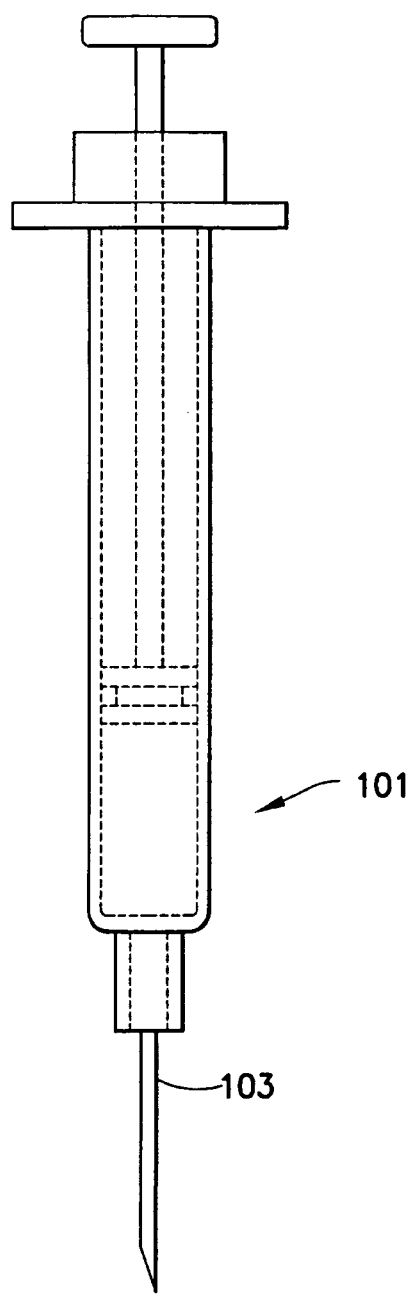
FIG. 1 is a front elevational view of a syringe.

In an exemplary embodiment of the present invention shown in FIGS. 4-9, a drug delivery device 201 injects insulin or other medicaments intradermally at high pressures. A needle hub 202, in which an intradermal needle 203 is rigidly fixed, is attached to an end 212 of a cartridge (medicament container) 211 disposed in the housing 205 of the device 201. Preferably, the needle 203 is an intradermal needle. Alternatively, the needle may be a subcutaneous needle. Preferably, the needle is a small gauge needle, such as a 34 gauge needle. The drug delivery device according to exemplary embodiments of the present invention injects insulin, high viscosity medicaments, or other medicaments at high pressures.

Figure 5:
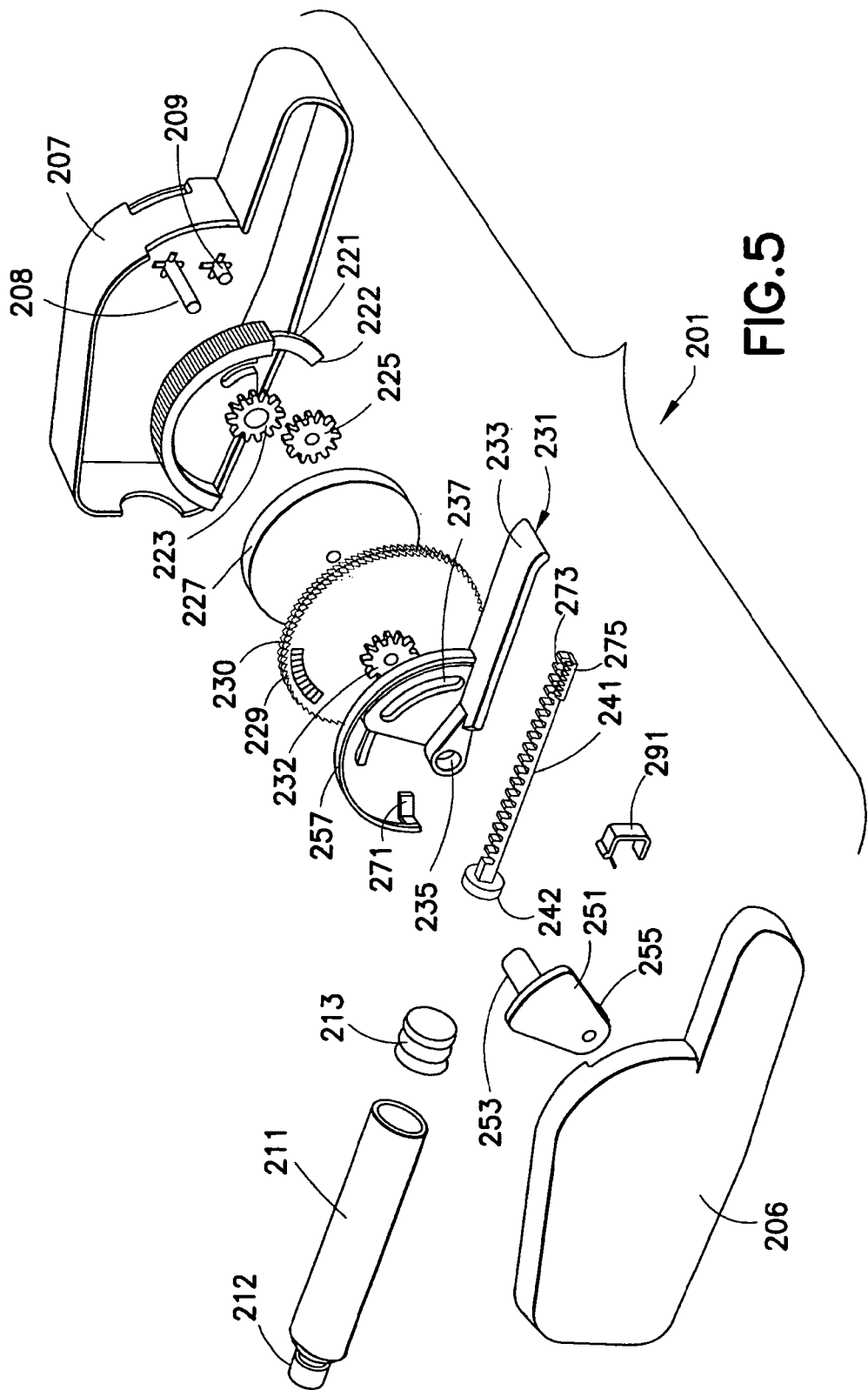
FIG. 5 is an exploded perspective view of the drug delivery device of FIG. 4.

A user dials a dose on the dose setting wheel 221, inserts the needle 203 into the skin at the injection site, and then injects the medicament dose by pressing the dose delivery lever 231. The drug delivery device 201 uses a system of levers and gears to translate a user input force into an injection pressure that is sufficient for an intradermal injection. As shown in FIG. 5, the housing 205 may have a first portion 206 and a second portion 207 that are connected together with the system of levers and gears disposed therein.

Figure 7:
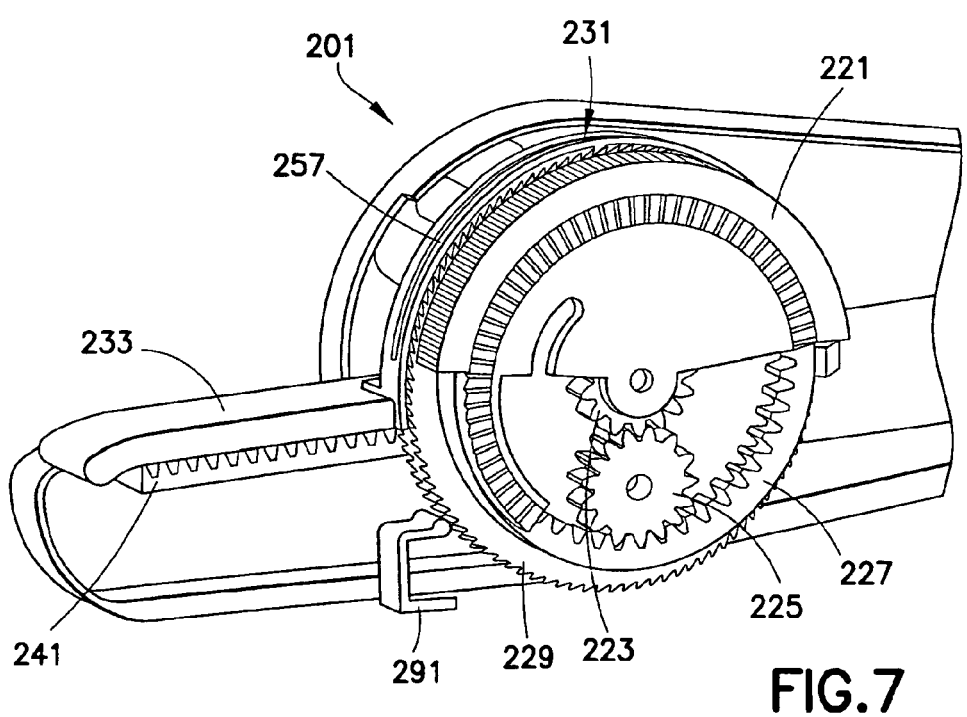

The medicament dose is set by rotating the dose setting wheel 221, which is coupled via planetary gears 223, 225, 227 and 229 to a rising dose delivery lever 231. The dose setting wheel 221 is rotated downwardly (counter-clockwise as shown in FIG. 7). The rotation of the dose setting wheel 221 rotates the dose setting gear 223, which rotates gear 225 (clockwise as shown in FIG. 7). The gear 225 has teeth that engage teeth 228 of gear 227. Gear 227 has a projection that engages the lever arm tab 271 such that the lever assembly 231 rotates with the gear 227. Gear 229 has teeth 230 on an outer surface thereof that correspond to the teeth on an inner surface of the flexible portion 257 of the lever assembly 231, such that the gear 229 is not rotated when the dose is being set. The gear 229 has a gear 232 fixed to a side thereof on a side of the gear 229 opposite to gear 227. The gear 232 engages a first plurality of teeth 273 of the movable rack 241.

Figure 6:
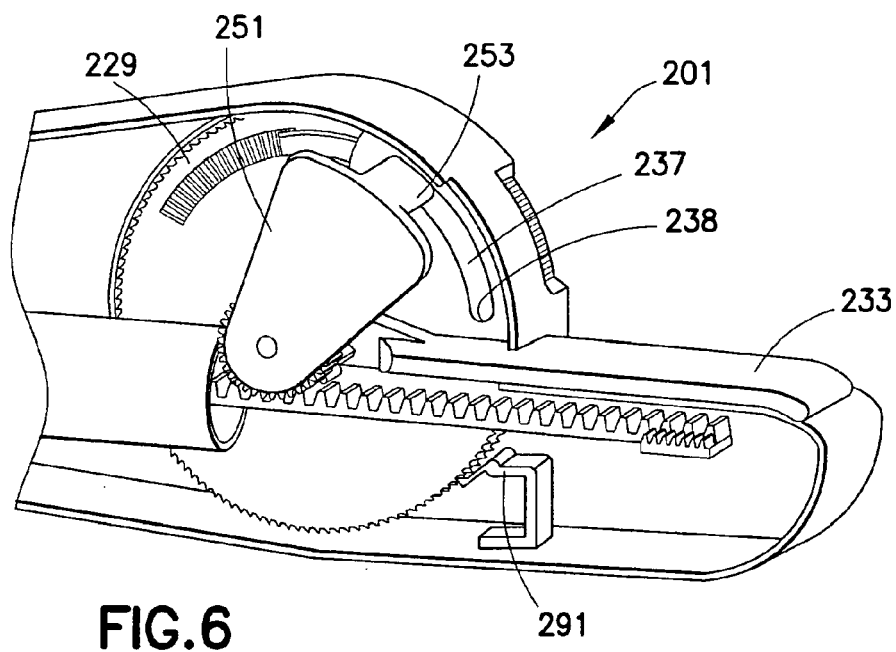
FIGS. 6-9 are perspective views in cross section of the drug delivery device of FIG. 4.
Figure 8:
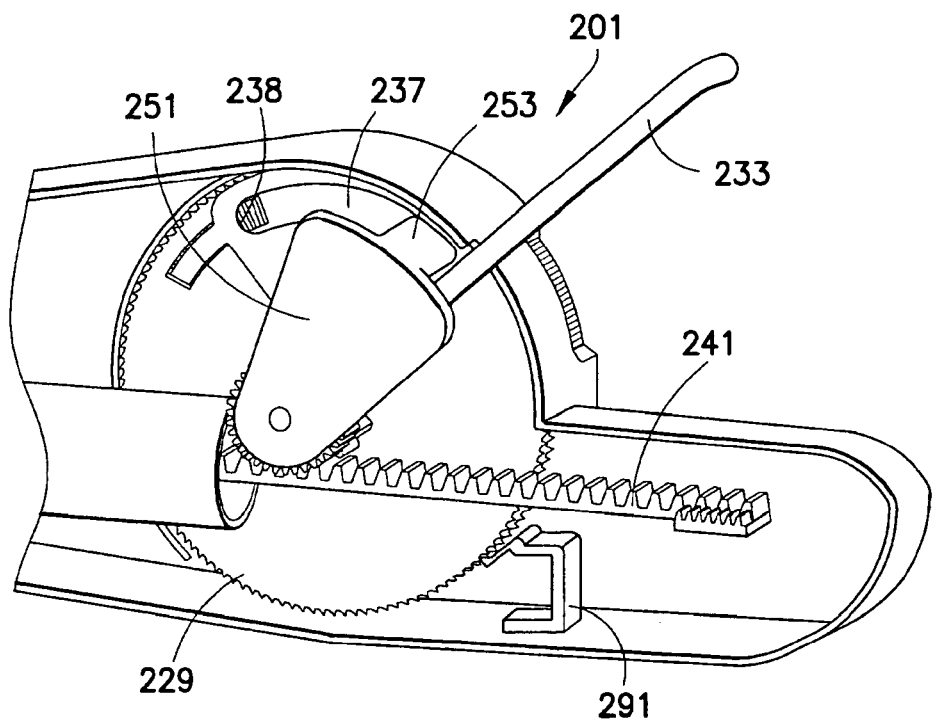
Figure 9:
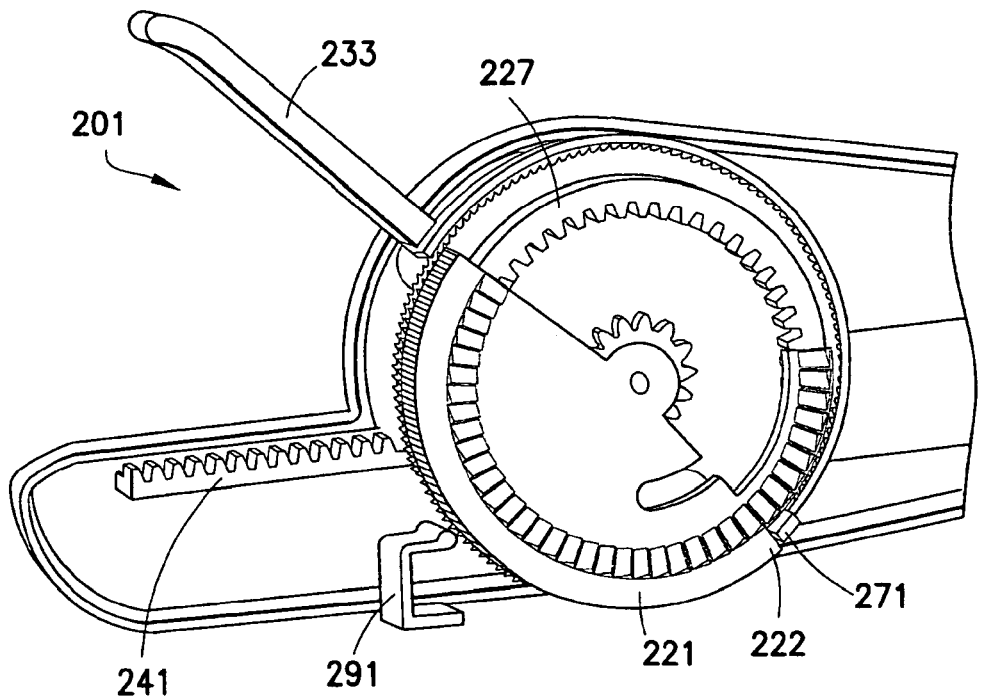
Figure 10A:
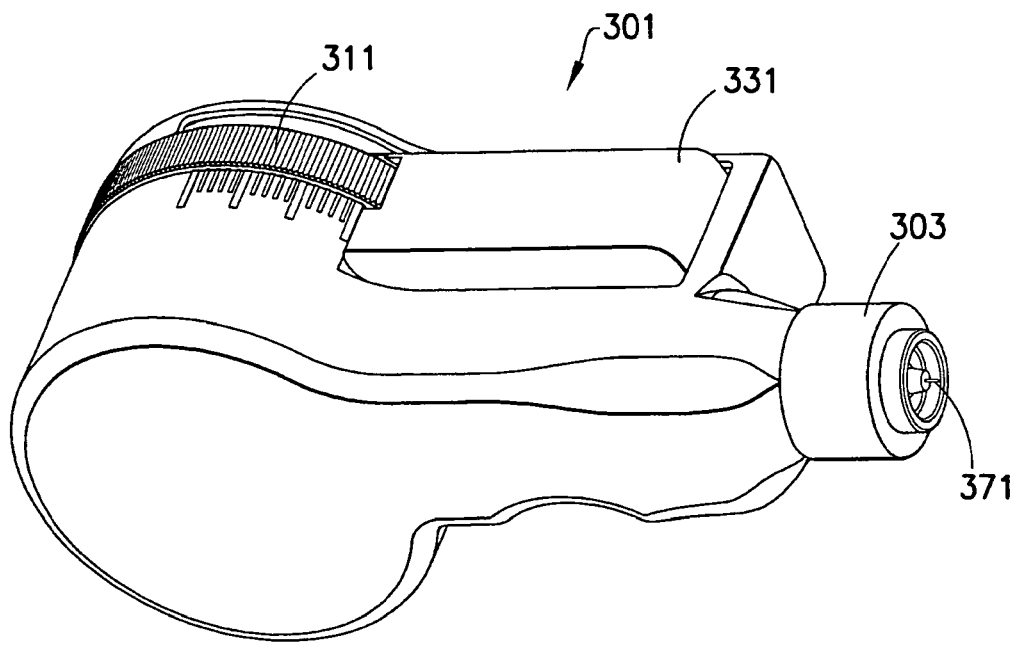
FIGS. 10A-10B are perspective views of a drug delivery device according to another exemplary embodiment of the present invention.
Figure 10B:
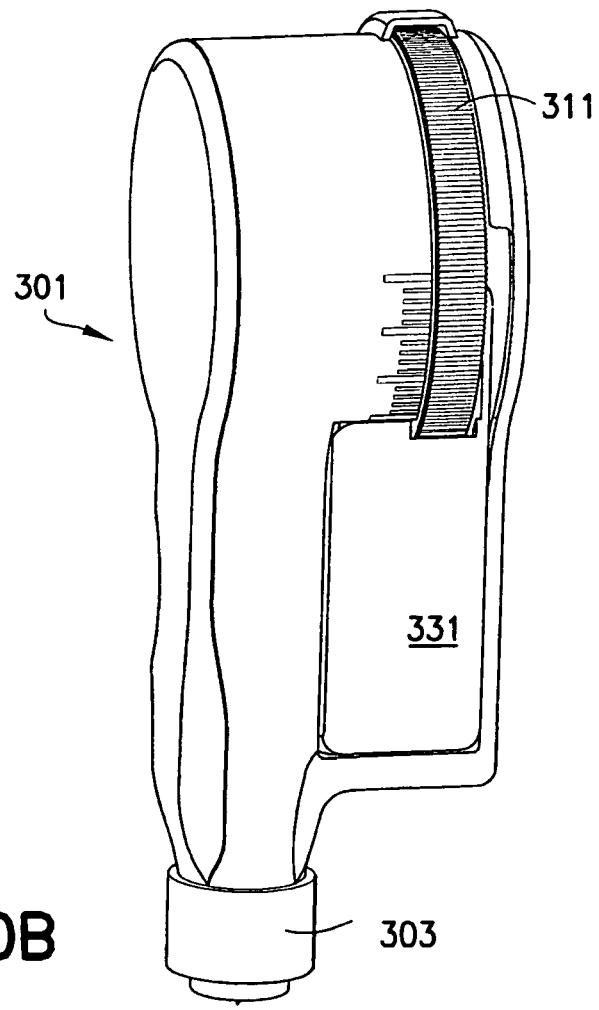

A lever assembly 231 includes a lever arm 233, which is in a first position as shown in FIGS. 6 and 7 and in a second position as shown in FIGS. 8 and 9. When the lever arm 233 is in the first position the medicament dose may be set, and when the lever arm 233 is in the second position the medicament dose may be delivered. A flexible portion 257 is connected to the lever arm 233. Preferably, a portion of the lever assembly 231, for example, the flexible portion 257, is substantially semi-circular, as shown in FIG. 5. An inner surface of the flexible portion 257 has teeth that engage the teeth 230 of gear 229. The teeth of the flexible portion 257 extend in the same direction as the teeth of the gear 229 such that the gear 229 only rotates with the lever arm 233 during the injection of the medicament dose, i.e., when the lever arm 233 is rotated counter-clockwise as shown in FIG. 9. The gear 229 does not rotate with the lever arm 233 when the lever arm rotates clockwise as shown in FIG. 9. A ratchet pawl 291 may be disposed in the housing 205 that engages the gear 229 to prevent rotation of the gear 229 during setting of the medicament dose. The ratchet pawl 291 allows rotation of the gear 229 in only one direction (clockwise as shown in FIGS. 6 and 8).

The movable rack 241 is engaged by the gear 232, such that rotation of the gear 232 moves the rack 241 through the cartridge 211 to deliver the medicament dose. A longitudinal central axis of the lever arm 233 intersects a centerline of the gear 232 and a portion of the lever assembly 231 is concentric with the gear 232. An end of the rack 242 engages a stopper 213 disposed in the cartridge 213. Movement of the rack 242 pushes the stopper through the cartridge 211. The medicament dose corresponds to the distance traveled by the stopper 213 through the cartridge.

Gears 223, 227, 229 and 232 are rotatably disposed on a first shaft 208. The lever assembly and dose limiting member 251 are also rotatably disposed on the first shaft. The gear 225 is disposed on a second shaft 209.

When the medicament dose is set, the lever arm 233 is in the second position as shown in FIGS. 8 and 9. To inject the medicament dose, the user depresses the lever arm 233, which is returned to the first position (FIGS. 6 and 7) as it rotates the gear 235. Rotation of the gear 235 advances the rack 241, thereby moving the stopper 213 through the cartridge 211. The user force is amplified by the lever arm 233 of the dose delivery lever 231, which is connected to the small gear 235, together creating enough mechanical advantage to allow for user medicament injections at the high pressures required for intradermal delivery.

A dose limiting component 251 engages the dose delivery lever 231 and the rack 241 to ensure correct positioning. The dose limiting component 251 has a dose limiting tab 253 that engages a groove 237 of the dose delivery lever 231. The groove 237 has a first end 238 and a second end 239. The dose limiting component 251 has a gear 255 that engages a second plurality of teeth 275 disposed on the rack 241. The dose limiting component 251 prevents dose setting when the drug volume is limited. When the available medicament remaining the cartridge 211 is less than a predetermined amount, the gear 255 engages the second plurality of teeth 275 of the rack 241, thereby rotating the dose limiting tab 253 to the first end 238 of the groove 237 when the lever arm 233 is in the first position. When an additional medicament dose is attempted to be set, the dose limiting tab 253 abuts the first end 238 of the groove 237 and prevents rotation of the lever arm 233. Accordingly, another medicament dose is prevented from being set.

Figure 2:
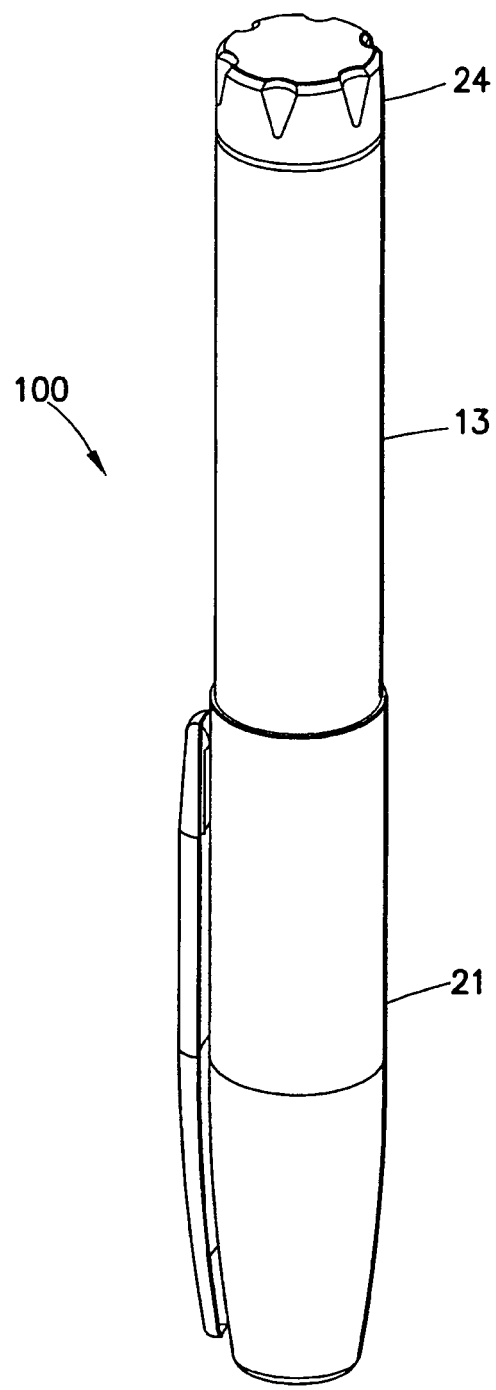
FIG. 2 is a perspective view of a drug delivery pen.
Figure 3:
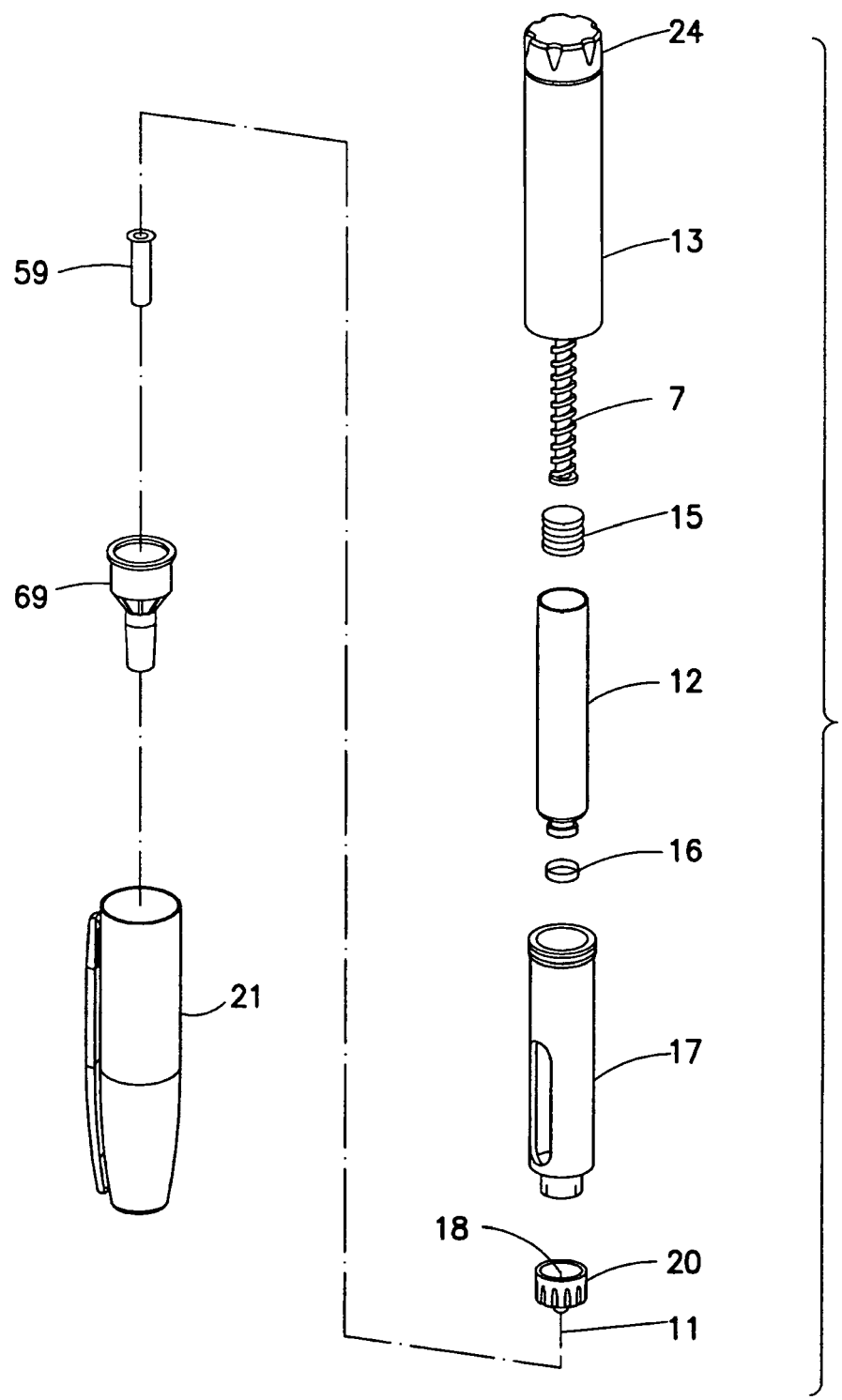
FIG. 3 is an exploded perspective view of the drug delivery pen of FIG. 2.
Figure 4:
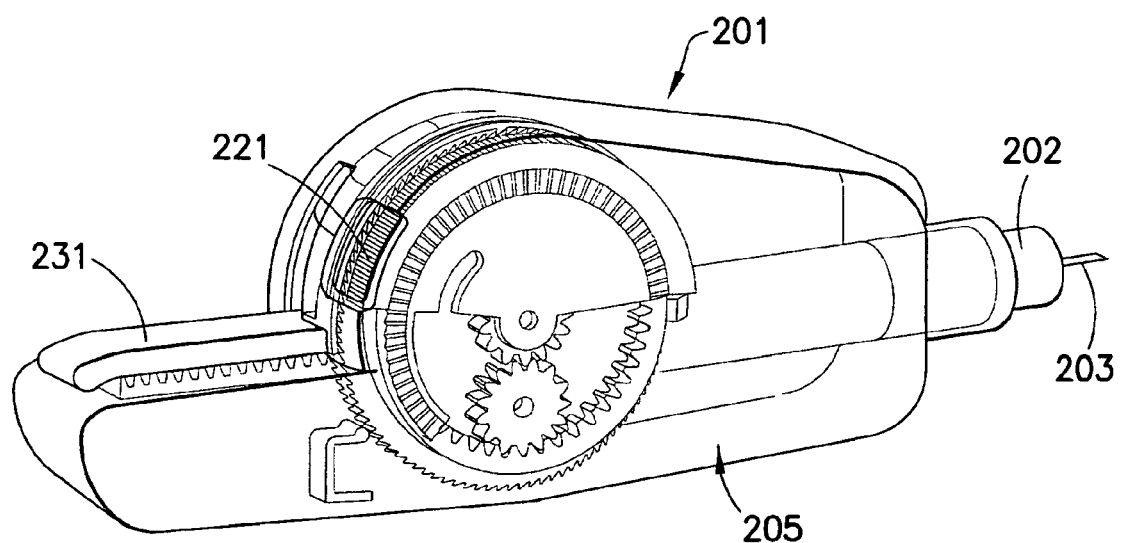
FIG. 4 is a perspective view of a drug delivery device according to an exemplary embodiment of the present invention.

The dose set mechanism features a planetary gear 225 to increase the distance between unit increments, thereby allowing the user to set the dose at (angle) increments similar to those of a current drug delivery pen 100 (FIGS. 2 and 3). A flexible portion 257 of the lever assembly has ratchet teeth, thereby enabling the user to correct the dose and converting the linear user force into a torque, which then drives the pinion 229 that advances the rack 241. The dose setting wheel 221 is rotated in a direction opposite from the direction the dose setting wheel 221 was rotated to set the dose (clockwise in FIG. 9 to correct the medicament dose). The protrusion 222 of the dose setting wheel 221 engages the lever arm tab 271 such that the lever arm 233 rotates with the dose setting wheel, i.e., the lever arm is rotated counterclockwise as shown in FIG. 9. The flexibility of the flexible portion 257 separates the teeth on the inner surface of the flexible portion 257 from the teeth of the gear 229 such that the gear 229 is not rotated with the lever arm 233. Accordingly, the rack 241 is not moved when the medicament dose is corrected.

In a preferred embodiment, for a given user force, $F_1$, a dose delivery lever arm, $L_1$, a pinion radius and second lever arm, $L_2$, the force multiplication is achieved using the following relationships: $F_1 \times L_1 = F_2 \times L_2$.

Therefore, for this preferred embodiment, the force multiplier $M_f$, $F_1/F_2$ becomes the ratio of the areas, $L_2/L_1 = M_f = 40/4.5 = 8.9$.

Therefore, using gear ratios and lever advantages, an approximately eight to nine force multiplication ($M_f$) may be achieved.

A drug delivery device 301 in accordance with another exemplary embodiment of the present invention is shown in FIGS. 10-28. The drug delivery device 301 is adapted to set a dose, deliver the dose, and track the dose.

The system of levers and gears are disposed in a housing 302 of the drug delivery device 301. A hub 303 is connected to the housing 302. A needle 304 is rigidly fixed in the housing 302. The needle 304 is in fluid communication with a medicament cartridge 351.

A dose set wheel 311 has a portion accessible through the housing 302 for setting the medicament dose. A dose set gear 313 is fixed to the dose set wheel 311. A dose set planet gear 315 is rotatably engaged with the dose set gear 313, which is fixed to a dose set internal gear 317. An outer surface of the internal gear 317 has a plurality of teeth for engaging with a flexible portion 332 of the lever assembly 331, as shown in FIG. 16.

Figure 11A:
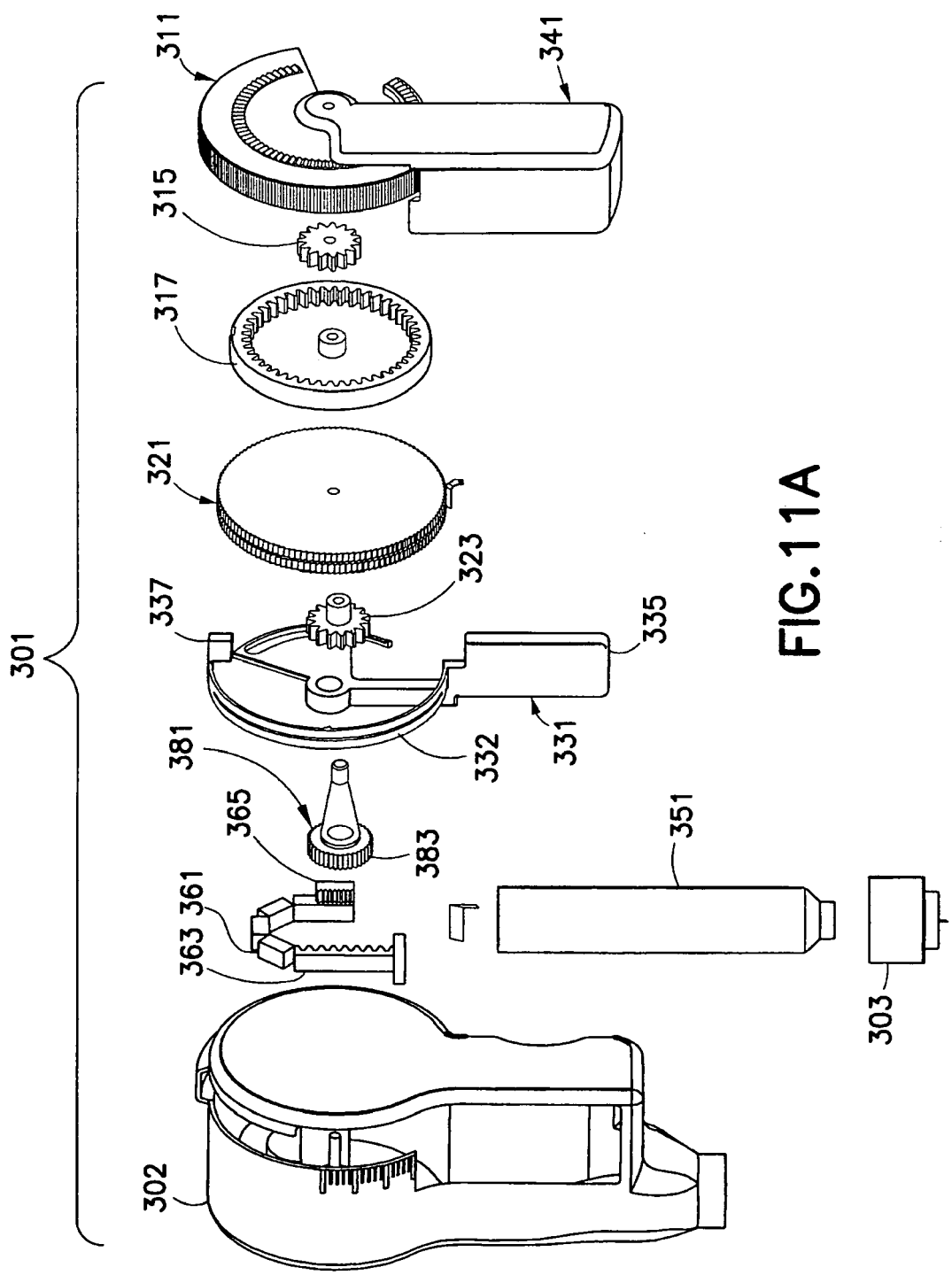
FIGS. 11A and 11B are exploded perspective views of the drug delivery device of FIGS. 10A-10B.
Figure 11B:
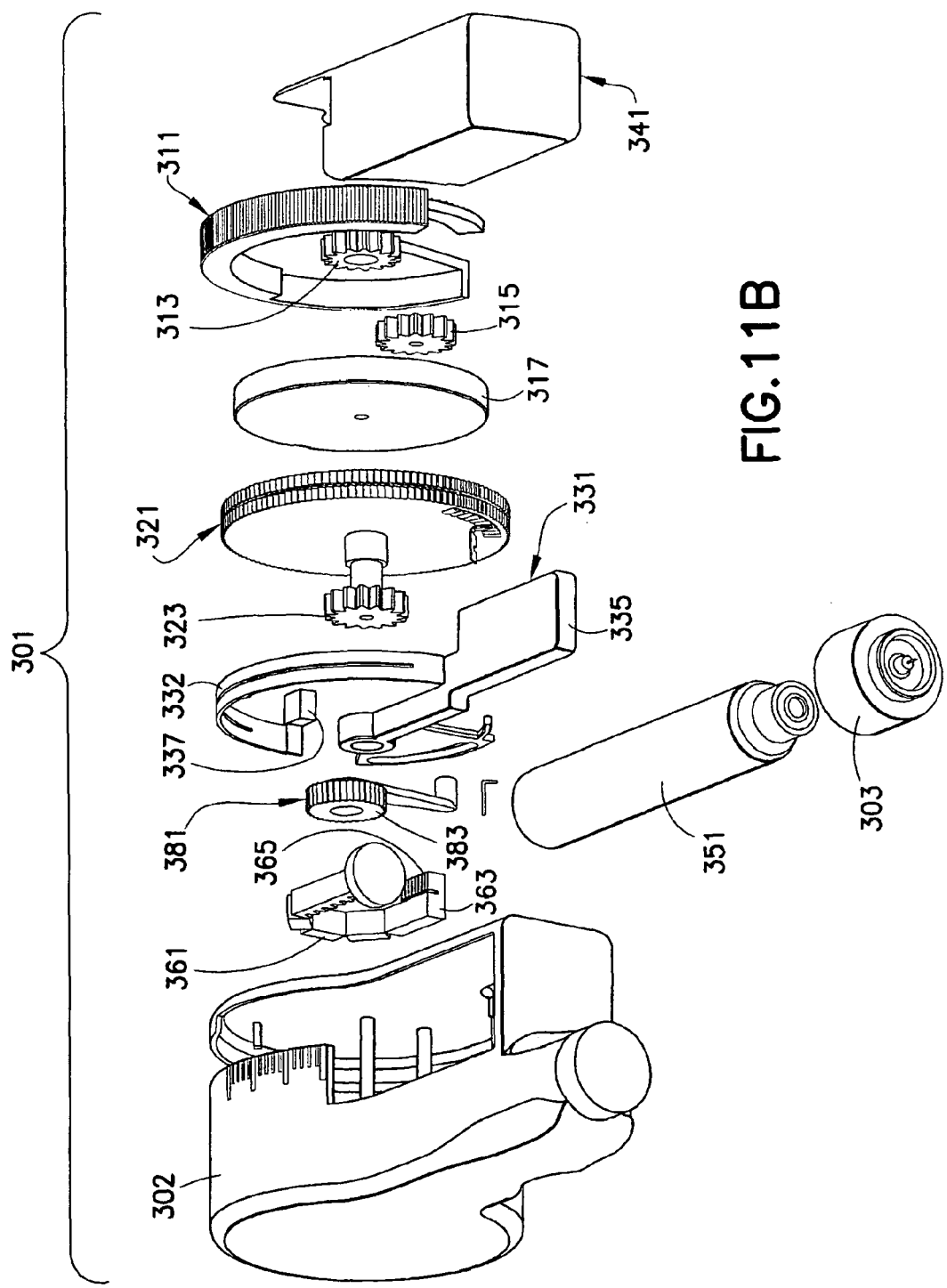
Figure 13:
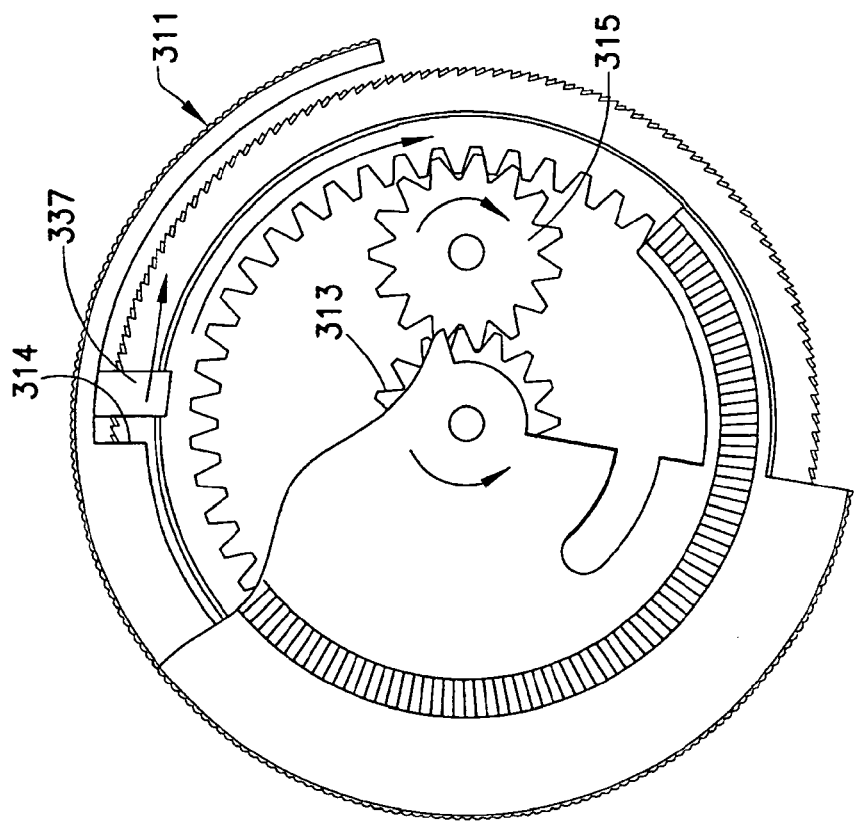
FIGS. 12-16 illustrate dialing a dose with the drug delivery device of FIGS. 10A-10B.
Figure 12:
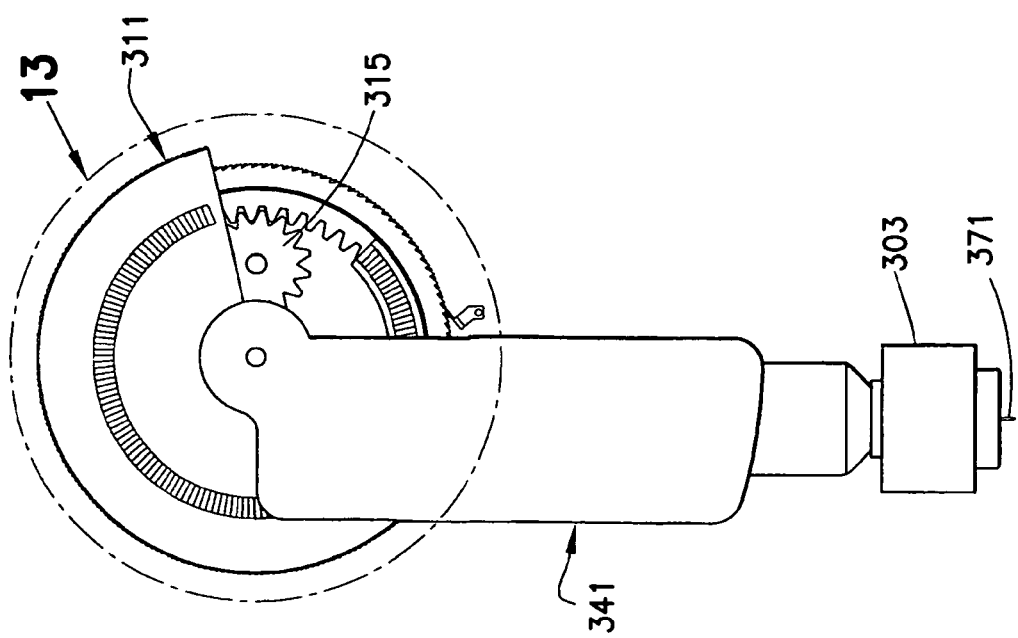
Figure 14:
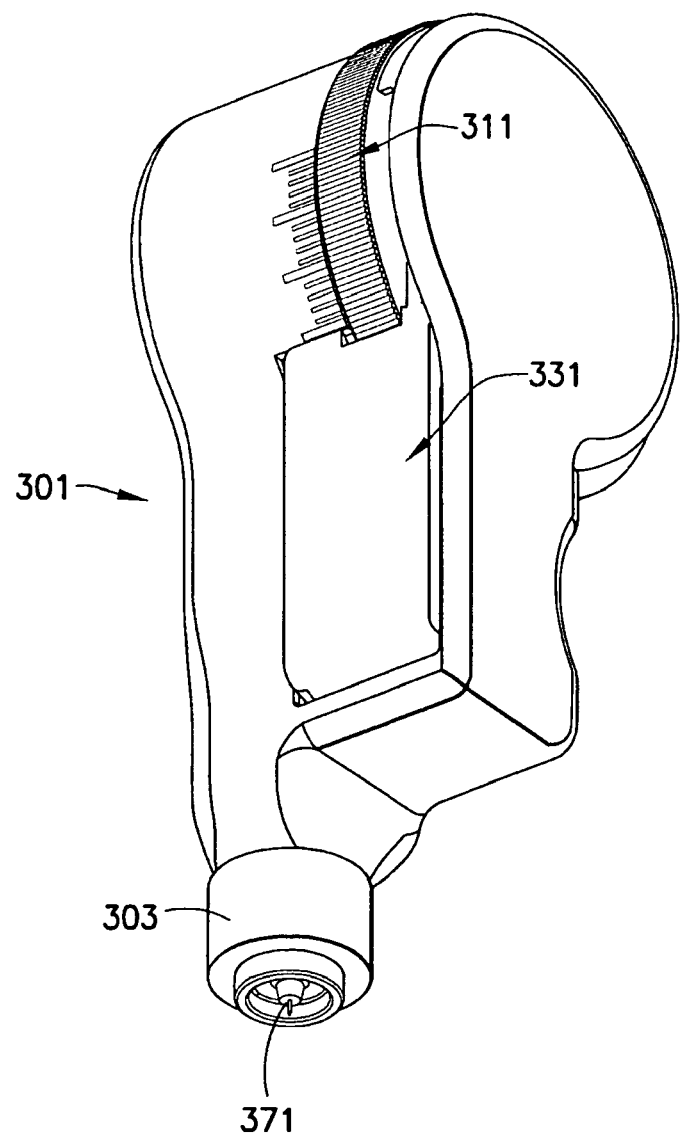
Figure 16:
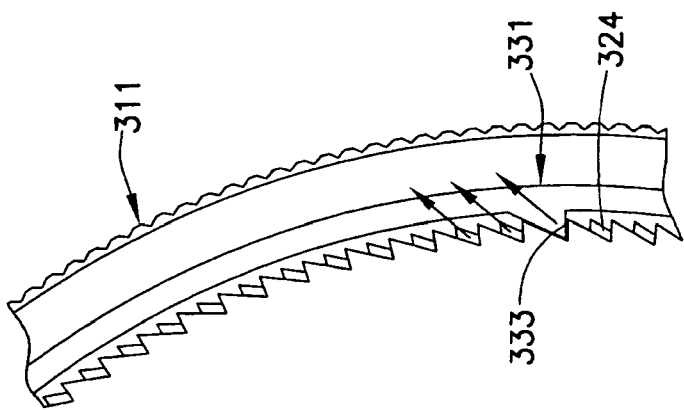
Figure 19:
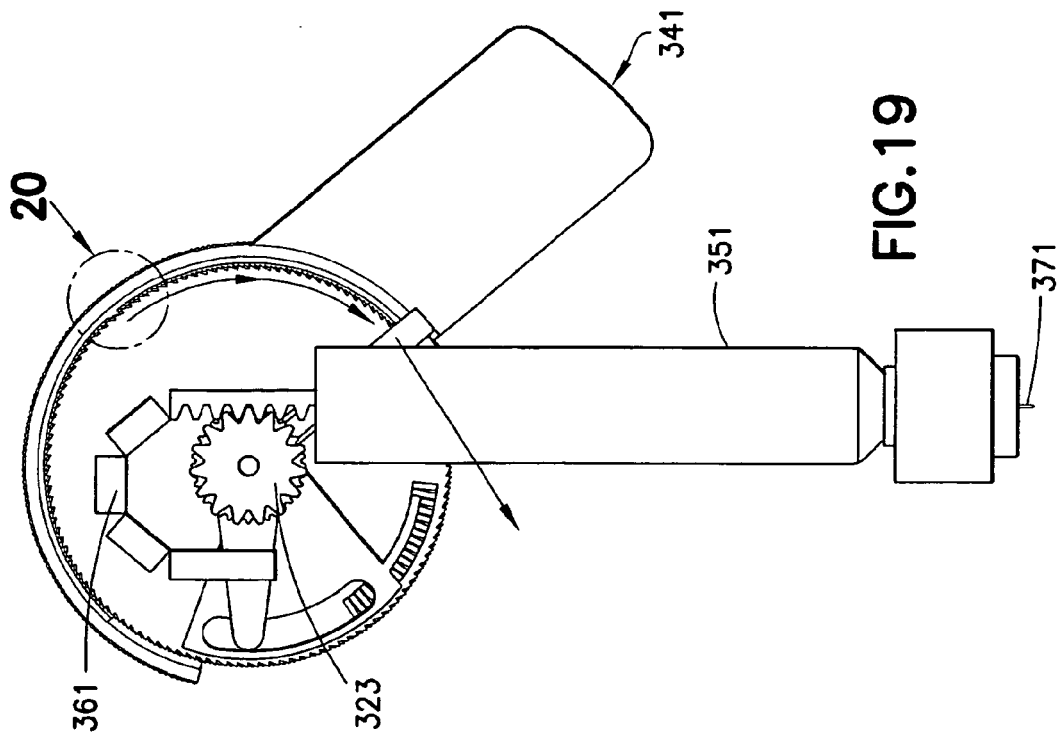
Figure 22:
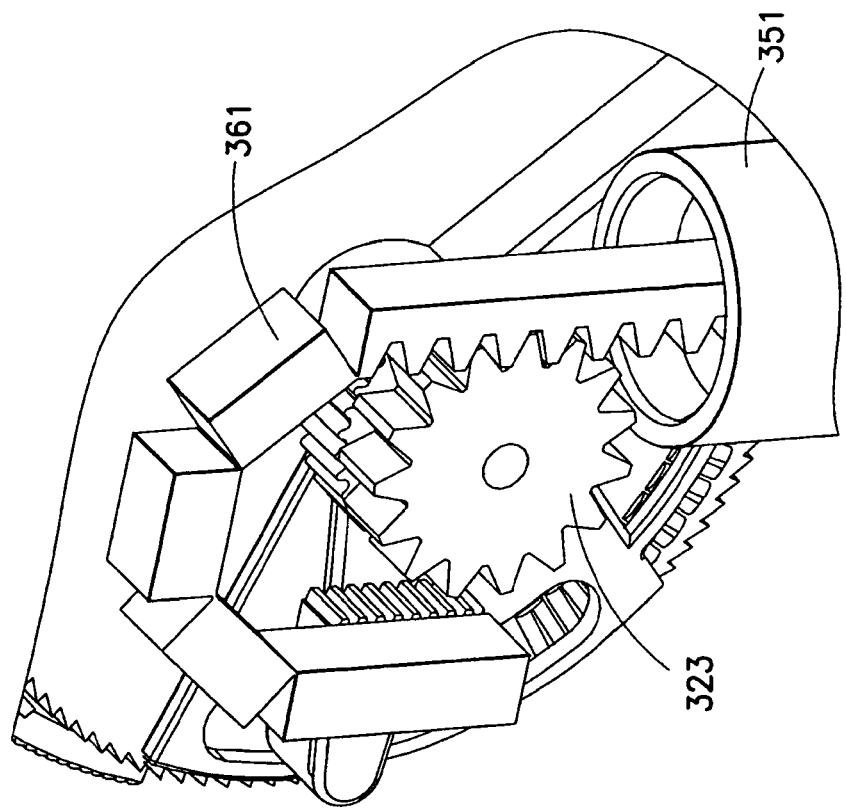
Figure 21:
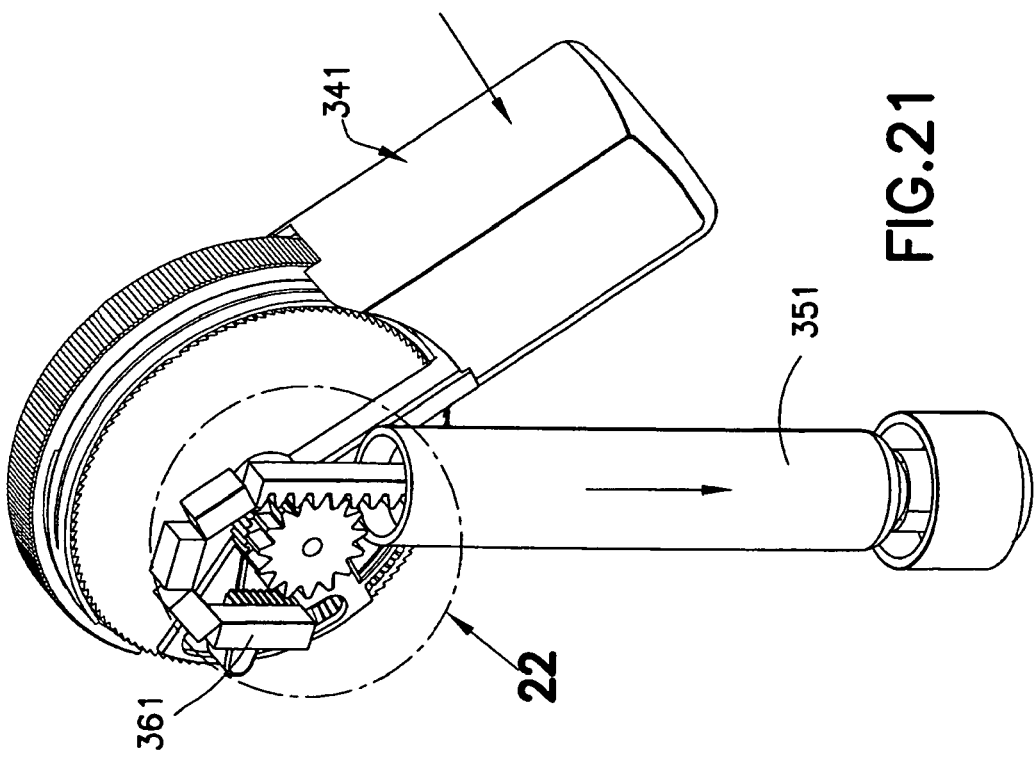

As shown in FIGS. 12-16, a medicament dose is dialed in the drug delivery device 301. The dose set gear 313 of the dose set wheel 311 is rotatably engaged with the dose set planet gear 315. Accordingly, rotation of the dose set wheel 311 rotates the dose set planet gear 315. The dose set planet gear 315 is connected to the dose set internal gear 317, which in turn rotates the lever assembly 331. As shown in FIG. 13, a lever tab 337 of the lever assembly 331 is engaged with the dose set internal gear 317. The flexible portion 332 of the lever assembly 331 clicks over the ratchet wheel 321, as shown in FIG. 16, and moves the lever arm 335 and the lever button 341 from a first position (FIG. 15) to a second position (FIG. 19). Accordingly, the ratchet wheel 321 is not rotated such that the rack 361 also does not rotate when the medicament dose is being set. As shown in FIG. 11, the rack 361 is curved when the cartridge 351 is substantially full of medicament.

FIGS. 17 and 18 illustrate correcting a dose on the drug delivery device 301. The dose set wheel 311 is rotated in a direction opposite to the direction in which the dose set wheel is rotated when setting the dose. As shown in FIG. 13, the lever arm tab 337 is engaged by a protrusion 314 of the dose setting wheel 311 when the dose is being corrected. As shown in FIG. 13, the dose setting wheel is rotated clockwise when the dose is being corrected. The engagement of the protrusion 314 with the lever arm tab 337 causes the flexible portion 332 of the lever assembly 331 to flex, such that the flexible portion separates from the ratchet wheel 321, thereby rotating the lever 331 assembly toward the first position.

Figure 15:
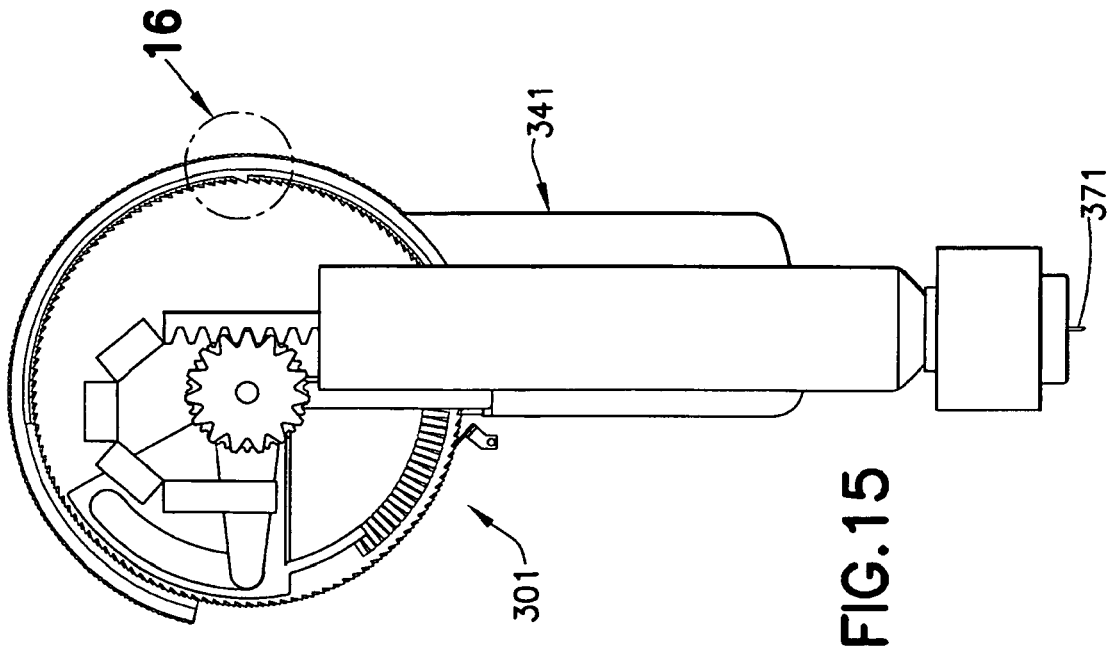
Figure 20:
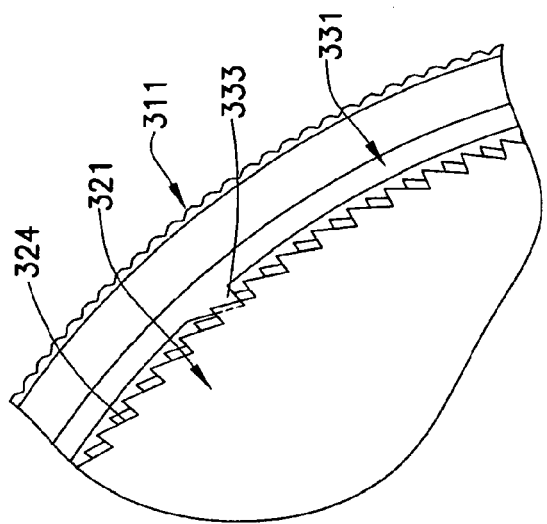
FIGS. 19-22 illustrate delivering a dose with the drug delivery device of FIGS. 10A-10B.

FIGS. 19-22 illustrate dose delivery with the drug delivery device 301. To deliver the dose, the lever button 341 is pushed inwardly toward the cartridge 351 from the second position (FIG. 19) to the first position (FIG. 15). A portion of the lever assembly 331 is concentric with a gear 323. Movement of the lever button 341 rotates the lever assembly 331, thereby rotating the ratchet wheel 321 engaged with the flexible portion 332. Teeth 324 of the ratchet wheel 321 engage the teeth 333 of the flexible portion 332, as shown in FIG. 20. Rotation of the ratchet wheel 321, in turn, rotates the gear 323 connected to the ratchet wheel 321. The gear 323 is engaged with the rack 361 such that rotation of the gear 323 drives the rack 361 into the plunger or stopper (213 of FIG. 5) disposed in the cartridge 351. The plunger then drives the medication through the needle 371 to intradermally deliver the dose.

Figure 26:
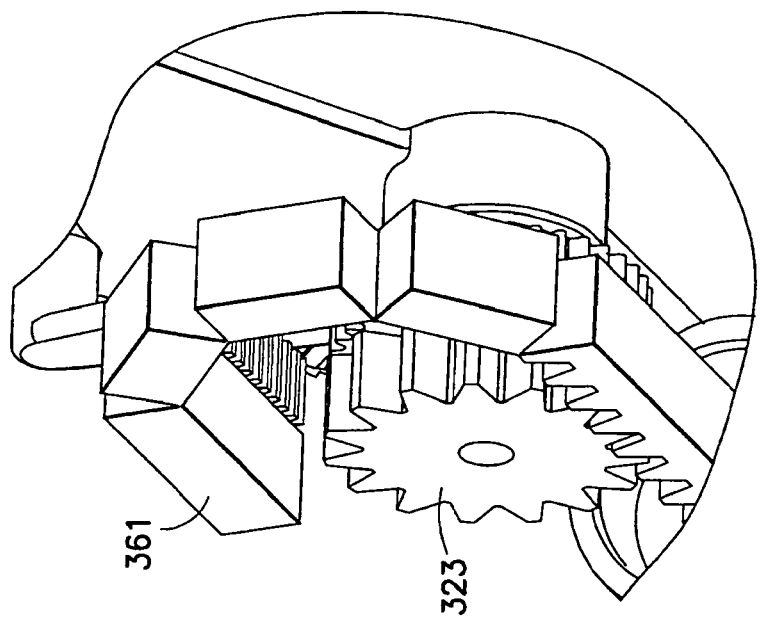
Figure 25:
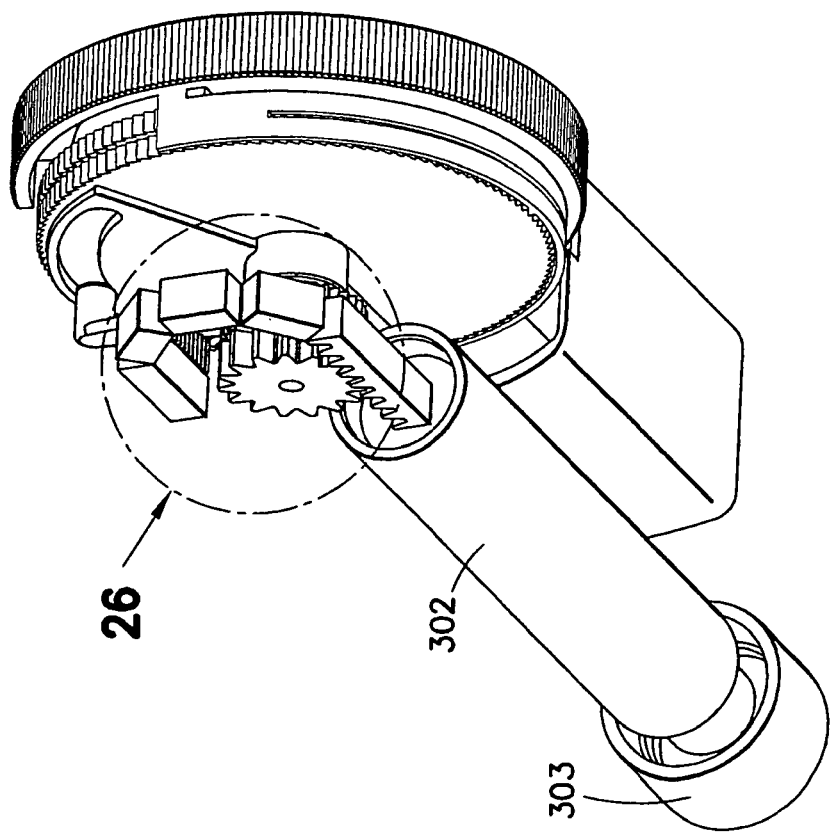

FIGS. 23-28 illustrate dose tracking with the drug delivery device 301. The dose limit gear 383 may be set to engage when 30 units of medication remain in the cartridge 351, thereby preventing dose setting beyond the available amount medication. When a sufficient amount of medication remains in the cartridge 351 to set a dose, the rack 361 and gear 323 of the ratchet wheel 321 are engaged, as shown in FIGS. 23, 25 and 26. When an insufficient amount of medication remains in the cartridge, the rack 351 engages both the gear 323 and the dose limit gear 383, as shown in FIGS. 24, 27 and 28, thereby preventing a dose from being set.

The rack 361 has a first plurality of teeth 363 and a second plurality of teeth 365, as shown in FIG. 11. The second plurality of teeth 365 is shorter than the first plurality of teeth 363. The gear 323 engages the first plurality of teeth 363 and the dose limit gear 381 engages the second plurality of teeth 365. The dose limit member 381 has a dose limit tab 385 that is received within a groove 336 of the lever assembly 331, as shown in FIG. 23. When the dose limit gear 383 is rotated by the second plurality of teeth 365 of the rack 361, the dose limit tab 385 is moved from the first end 338 to the second end 339 of the groove 336. When the dose limit tab 385 engages the second end 339 of the groove 336, the lever assembly 331 is prevented from moving, thereby preventing a medicament dose from being set.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. A drug delivery device, comprising:
 a housing enclosing a cartridge, said cartridge storing a medicament;
 a needle communicating with said cartridge for injecting a medicament dose;
 a rack movably disposed in said cartridge, said rack being engageable with a stopper for expelling the medicament dose from the cartridge, said stopper being collinear with said rack; and
 a lever assembly having a lever arm rotatably connected to a lever gear, said lever gear being engaged with said rack such that rotation of said lever arm rotates said lever gear during injection of the medicament dose, thereby moving said rack and said stopper through said cartridge to deliver the medicament dose, wherein
 a portion of said lever assembly is concentric with said lever gear.

2. The drug delivery device according to claim 1, wherein a longitudinal central axis of said lever arm intersects a centerline of said lever gear.

3. The drug delivery device according to claim 1, wherein said portion of said lever assembly is substantially semicircular.

4. A drug delivery device, comprising:
 a housing enclosing a cartridge, said cartridge storing a medicament;
 a needle communicating with said cartridge for injecting a medicament dose;
 a rack movably disposed in said cartridge, said rack being engageable with a stopper for expelling the medicament dose from the cartridge; and
 a lever assembly having a lever arm connected to a lever gear, said lever gear being engaged with said rack such that rotation of said lever arm rotates said lever gear during injection of the medicament dose, thereby moving said rack and said stopper through said cartridge to deliver the medicament dose, wherein
 a dose setting wheel is rotated to set the medicament dose, said dose setting wheel being connected to said lever arm such that when said dose setting wheel is rotated to set the medicament dose said lever arm moves from a first position to a second position.

5. The drug delivery device according to claim 4, wherein a plurality of gears are disposed between said dose setting wheel and said lever arm.

6. The drug delivery device according to claim 4, wherein said lever assembly has a lever tab that engages said dose setting wheel such that rotation of said dose setting wheel in a direction opposite to that in which the medicament dose was set moves said lever arm, thereby correcting the medicament dose.

7. The drug delivery device according to claim 4, wherein said lever assembly has a flexible portion allowing the medicament dose to be corrected.

8. The drug delivery device according to claim 4, wherein said lever gear does not rotate when said lever arm is moved from said first position to said second position.

9. A drug delivery device, comprising:
 a cartridge for storing a medicament;
 a needle communicating with said cartridge for injecting a medicament dose;
 a rack movably disposed in said cartridge, said rack being engageable with a stopper for expelling the medicament dose from the cartridge; and
 a lever assembly having a lever arm connected to a lever gear, said lever gear being engaged with said rack such that rotation of said lever arm rotates said lever gear during injection of the medicament dose, thereby moving said rack and said stopper through said cartridge to deliver the medicament dose, wherein
 a dose limiting member has a dose limiting tab and a dose limiting gear, said dose limiting tab being received by a groove in said lever assembly and said dose limiting gear rotatably engaging said rack.

10. The drug delivery device according to claim 9, wherein
 said groove has a first end and a second end, when said rack moves during the injection said dose limiting gear rotates such that said dose limiting tab moves from said first end of said groove to said second end such that when said dose limiting tab reaches said second end of said groove another medicament dose is prevented from being set.

11. The drug delivery device according to claim 10, wherein
 said rack has a first plurality of teeth and a second plurality of teeth, said lever gear engaging said first plurality of teeth and said dose limiting tab engaging said second plurality of teeth.

12. The drug delivery device according to claim 11, wherein
 said second plurality of teeth have a shorter length than said first plurality of teeth.

13. A drug delivery device, comprising:
a housing enclosing a cartridge, said cartridge storing a medicament;
a needle communicating with said cartridge for injecting a medicament dose;
a rack movably disposed in said cartridge, said rack being engageable with a stopper for expelling the medicament dose from the cartridge, said stopper being collinear with said rack;
a lever assembly having a lever arm rotatably movable between a first position and a second position, said second position corresponding to when the medicament dose is set;
a ratchet wheel engaged with said lever assembly, said ratchet wheel having a ratchet gear being engaged with said rack such that rotation of said lever arm from said second position to said first position directly rotates said ratchet gear, thereby moving said rack and said stopper through said cartridge to deliver the medicament dose, wherein a portion of said lever assembly is concentric with said ratchet gear.

14. A drug delivery device, comprising:
a housing enclosing a cartridge, said cartridge storing a medicament;
a needle communicating with said cartridge for injecting a medicament dose;
a rack movably disposed in said cartridge, said rack being engageable with a stopper for expelling the medicament dose from the cartridge;
a lever assembly having a lever arm movable between a first position and a second position, said second position corresponding to when the medicament dose is set;
a ratchet wheel engaged with said lever assembly, said ratchet wheel having a ratchet gear being engaged with said rack such that movement of said lever arm from said second position to said first position rotates said ratchet gear, thereby moving said rack and said stopper through said cartridge to deliver the medicament dose, wherein
a dose setting wheel is rotated to set the medicament dose, said dose setting wheel being connected to said lever assembly such that when said dose setting wheel is rotated to set the medicament dose said lever arm moves from said first position to said second position.

15. The drug delivery device according to claim 14, wherein
said lever assembly has a lever tab that engages said dose setting wheel such that rotation of said dose setting wheel in a direction opposite to that in which the medicament dose was set moves said lever arm, thereby correcting the medicament dose.

16. The drug delivery device according to claim 15, wherein
said lever assembly has a flexible portion such that a flexible portion of said lever assembly separates from said ratchet wheel, thereby allowing the medicament dose to be corrected.

17. The drug delivery device according to claim 14, wherein
said ratchet gear does not rotate when said lever arm is moved from said first position to said second position.

18. The drug delivery device according to claim 14, wherein
said rack is curved when said cartridge is substantially full of medicament.

19. A drug delivery device, comprising:
a cartridge for storing a medicament;
a needle communicating with said cartridge for injecting a medicament dose;
a rack movably disposed in said cartridge, said rack being engageable with a stopper for expelling the medicament dose from the cartridge;
a lever assembly having a lever arm movable between a first position and a second position, said second position corresponding to when the medicament dose is set;
a ratchet wheel engaged with said lever assembly, said ratchet wheel having a ratchet gear being engaged with said rack such that movement of said lever arm from said second position to said first position rotates said ratchet gear, thereby moving said rack and said stopper through said cartridge to deliver the medicament dose, wherein
a dose limiting member has a dose limiting tab and a dose limiting gear, said dose limiting tab being received by a groove in said lever assembly and said dose limiting gear rotatably engaging said rack.

20. The drug delivery device according to claim 19, wherein
said groove has a first end and a second end, when said rack moves during the injection said dose limiting gear rotates such that said dose limiting tab moves from said first end of said groove to said second end such that when said dose limiting tab reaches said second end of said groove another medicament dose is prevented from being set.

21. The drug delivery device according to claim 20, wherein
said rack has a first plurality of teeth and a second plurality of teeth, said ratchet gear engaging said first plurality of teeth and said dose limiting tab engaging said second plurality of teeth.

22. The drug delivery device according to claim 21, wherein
said second plurality of teeth is shorter than said first plurality of teeth.

* * * * *